US005570698A

United States Patent [19]
Liang et al.

[11] Patent Number: 5,570,698
[45] Date of Patent: Nov. 5, 1996

[54] SYSTEM FOR MONITORING EYES FOR DETECTING SLEEP BEHAVIOR

[75] Inventors: Cheng-Chung Liang, Lawrenceville; Ming Fang, Cranbury; Ajit Singh, Plainsboro, all of N.J.

[73] Assignee: Siemens Corporate Research, Inc., Princeton, N.J.

[21] Appl. No.: 459,148

[22] Filed: Jun. 2, 1995

[51] Int. Cl.$^6$ .................................................. A61B 13/00
[52] U.S. Cl. .......................... 128/745; 340/575; 351/206; 351/211
[58] Field of Search ............................. 128/745; 351/206, 351/209, 211, 221; 340/573, 575

[56] References Cited

U.S. PATENT DOCUMENTS 5,360,971  11/1994  Kaufman et al. ................. 128/745 X

FOREIGN PATENT DOCUMENTS 2215040  9/1989  United Kingdom ................. 340/575

Primary Examiner—Angela D. Sykes
Assistant Examiner—Ryan Carter
Attorney, Agent, or Firm—Donald B. Paschburg

[57] ABSTRACT

A system for monitoring eyes of an individual includes a human interface for obtaining images of the individual and for providing feedback to the individual and a processor for analyzing the images. The processor transforms an image sequence into a one dimensional signal by extracting relevant features from the images. Analysis of the signal generated then occurs to detect sleepiness. Transformation of the image sequence includes eye localization, eye tracking and eye motion signal generation. The system takes advantage of the relatively high horizontal-contrast density of the eye region to determine eye positions in a greyscale image of a human face.

16 Claims, 9 Drawing Sheets

SYSTEM FOR MONITORING EYES FOR DETECTING SLEEP BEHAVIOR

BACKGROUND OF THE INVENTION

1. Field of the Invention

The present invention relates to determining eye positions and more particularly to a reliable, non-invasive system for monitoring an individual, processing images of the individual and providing feedback to the individual.

2. Description of the Prior Art

Monitoring of sleepiness and sleep has traditionally been of interest to psychologists and neurophysiologists studying behavioral effects of sleep deprivation, sleep disorders, etc. Recently, there has been a lot of interest in monitoring sleepiness and fatigue on the job—and the human error that results from it. Some categories of professionals that have directly stirred this interest are medical residents, truck and train drivers, airline pilots, air traffic controllers, assembly line workers involved in monotonous jobs, etc. The following examples and statistics are self explanatory: In 1978, a commercial airliner scheduled to land at Los Angeles International Airport passed over the airport at 32,000 feet and headed out over the pacific. Flying on autopilot, the plane was about 100 miles out to the sea before the air traffic controllers found a way to sound an alarm in the cockpit. The entire crew had fallen asleep on the flight deck. In the United States, an estimated total of 6,500 automobile related deaths every year—13 percent of the annual toll—are caused by drivers falling asleep at the wheel. Fatigue and human error remains the biggest cause of automobile accidents. While the safety of automobile drivers and passengers has been getting increased attention in recent years (air bags and anti-lock brakes are becoming available and affordable), car manufacturers have begun to look at fatigue sensing only recently. In a recent CNN survey of 1000 truck drivers, 3 out of 5 drivers admitted to have fallen asleep behind the wheel in the month preceding the survey. Truck drivers commonly exceed the maximum permitted 80 hours a week of driving.

While sociological implications of monitoring sleepiness and sleep on the job remain uncertain and need a serious consideration, technological progress is well on its way to make such monitoring possible. Frequently, an electroencephalogram (EEG) is used in conjunction with an electrooculogram (EOG) to measure eye movements and an electromyogram (EMG) to measure the muscle tonus in the chin. This is described in "Work Hours And Continuous Monitoring Of Sleep", Akerstedt, T., In Broughton, R. J., and Ogilvie, R. D., Sleep, Arousal and Performance, Birkhauser, Boston, 1991. Eye movements are particularly useful in detecting the accurate onset of sleep as described in "Eye Movements And The Detection of Sleep Onset", Ogilvie R. D., McDonagh, D. M. and Stone, S. N., Psychophysiology, Vol. 25, No. 1, pp. 81–91, 1988. Another alternative has been developed by Nissan which includes using distinctive steering patterns produced by a fatigued driver. This is discussed in "Electronic Applications For Enhancing Automotive Safety", Aono, S., Vehicle Electronics in the 90's: Proceedings of the International Congress on Transportation Electronics, pp. 179–186, Oct., 1990.

While technological advances have made EEG based monitoring of sleep quite convenient (portable EEG-sleep recorders of pocket size are available), it is essentially an invasive technique. The subject has electrodes attached to his/her head. In applications such as monitoring sleepy behavior of a car driver, a non invasive technique is more desirable. Visual monitoring of the eyes appears to have the promise of providing such a non invasive technique. Specifically of interest is the monitoring of drivers (of cars, trucks, trains, etc.) and the ability to raise an alarm when the driver appears sleepy. For visual monitoring, one obvious and natural choice is to use the motion of a person's eye to detect sleepy behavior. This approach must be done correctly and reliably.

The correlation between the behavior of the eye and sleep dates back to very early days of sleep research. Miles, in his seminal paper of 1929 wrote: ". . . the contrast between alertness and drowsiness is nowhere more evident than in the condition and behavior of the eye . . . " Miles filmed rolling eye movements during drowsiness and used them to characterize sleep. While some of the earlier work on monitoring the eyes was done visually (by recording movies of the eye on a film), it was soon replaced by EEG and EOG based monitoring.

Practically none of the current research on sleep behavior uses visual monitoring of the eyes. This is partly because of high variability in the correlation between external appearance of the eye and physiological stages of sleep, as well as because of unavailability of equipment that can provide quantitative data. However, based on observation of sleep subjects as well as interaction with some of the experts, the following statements can be made regarding the behavior of the eyes during alertness, sleepiness and onset of sleep:

1. In a state of alertness, human eyes blink. The average blink rate (average number of blinks per minute) varies significantly across individuals. Also, for a given alert individual, the blink rate can vary as a function of time, depending on factors such as nervousness. The blink duration (the time it takes for the eyelid to close and open again) is of the order of one third of a second.

2. The blink rate of the eye increases during sleepiness. In effort to fight sleep, the subjects often squint their eyes, and blink frequently. While the average blink rates of individuals differ significantly, there is a marked change of blink rate from alertness to sleepiness across the population. The blink rate can increase by a factor of two or more from alertness to sleepiness.

3. During sleepiness, the eyelids become heavy and behave sluggishly. The time it takes for eyelids to close during sleepiness is much longer than the blink duration; it is of the order of a few seconds (in the range of one to four seconds). At the onset of sleep, the eyelid may or may not open after it closes.

4. It is possible to be asleep with eyes open completely. A small fraction of the population exhibits this behavior.

5. Slow Eye Movements (SEM) appear during sleepiness and disappear at the beginning of behaviorally and physiologically defined sleep. This pattern is a consistent indicator of sleep onset over large populations.

For many visual monitoring and surveillance applications, it is important to determine human eye positions from an image sequence containing a human face. Once the human eye positions are determined, all of the other important facial features, such as positions of the nose and mouth, can easily be determined. The basic facial geometric information, such as the distance between two eyes, nose and mouth size, etc., can further be extracted. This geometric information can then be used for a variety of tasks, such as for recognizing a face from a given face database. The eye localization system can also be directly used for detecting the sleepy behavior of a car driver.

Some techniques exist for eye localization based on the Hough transform, geometry and symmetry checks and deformable models. Most of these techniques are not sufficiently robust against shape changes. These systems also require an extensive amount of computer processing time. Furthermore, none of these existing systems can locate eyes when the eyes are closed.

SUMMARY OF THE INVENTION

The present invention is a reliable, non-invasive system for monitoring the eyes of an individual which comprises a human interface as well as a processor. The human interface comprises, at a minimum, a camera for observing an individual and a warning system to alert the individual at the onset of sleep. The processor is used with the camera to transform an image sequence to a one dimensional signal by extracting relevant features from the images. The processor than analyzes the one-dimensional signal generated to detect sleepiness. Transforming the image sequence includes eye localization, eye tracking and eye motion signal generation. Eye localization utilizes filters that take advantage of the relatively high horizontal-contrast density of the eye region to determine eye positions in a greyscale image of a human face. The filters are a horizontal-contrast computation filter, a horizontal-contrast density determination filter, facial geometry reasoning and eye position determination.

BRIEF DESCRIPTION OF THE DRAWINGS

Figure one illustrates one embodiment of the present invention.

Figure two illustrates the processor utilized in the present invention.

Figure 1:
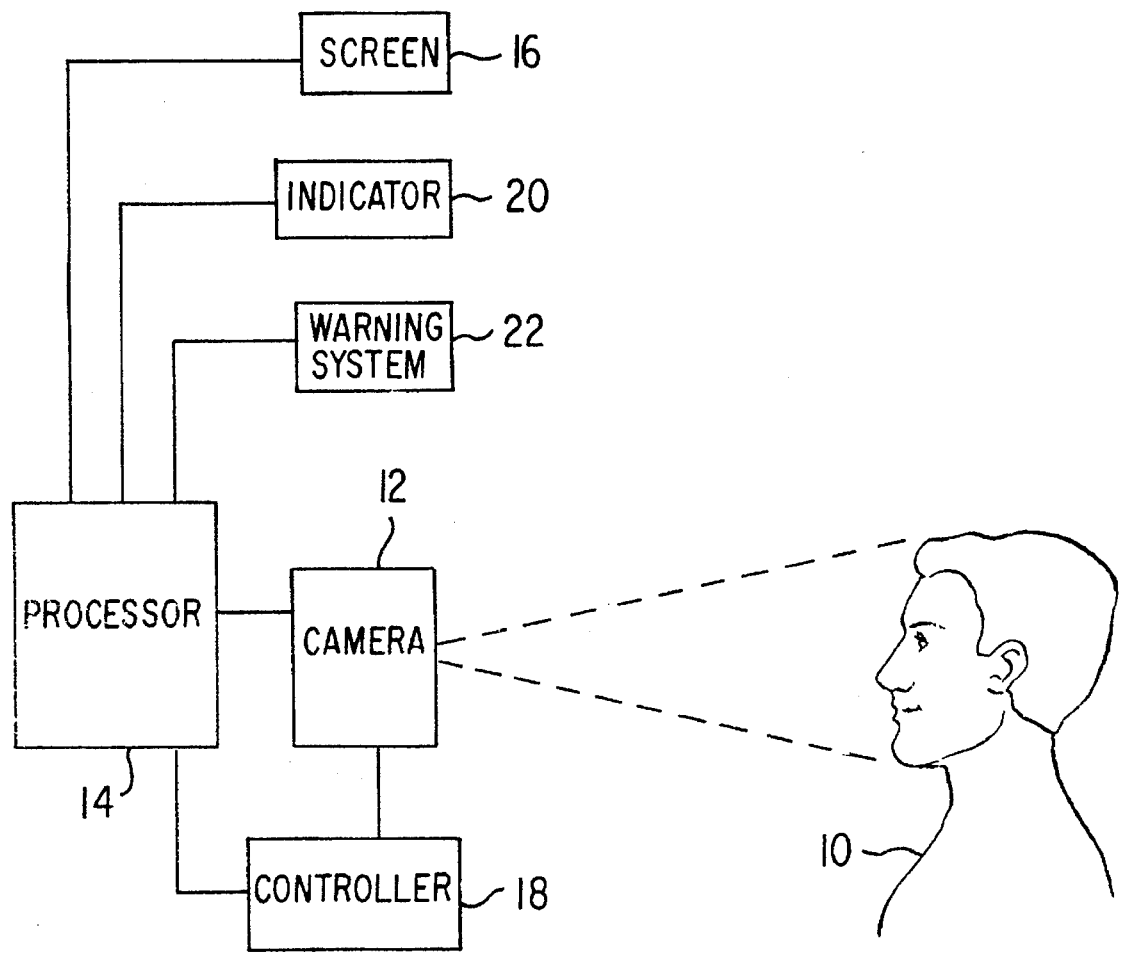

Figure three illustrates a flow diagram of the processing of the present invention.

Figure four illustrates a flow diagram of the eye localization filter of the present invention.

Figure five illustrates the effects of the eye localization filter of the present invention.

Figure six illustrates experimental results of the filtering of the present invention.

Figure seven illustrates locating the eye by using a greyscale eye template of the present invention.

Figure eight illustrates parts of an image sequence with the tracking box superimposed on the images.

Figure nine illustrates tracking and block difference measurement for the image sequence of figure eight.

Figure ten illustrates a normal eye blinking and the corresponding T and D curves.

Figure eleven illustrates a sequence when the person is sleepy and the corresponding T and D curves.

DETAILED DESCRIPTION OF THE INVENTION

To establish the system requirements for visual monitoring of human eyes, to detect sleepiness and sleep onset, certain assumptions must be made. The scenario in consideration for the system is the driver's compartment of a car or a truck, etc.

Lighting conditions inside a driver's compartment vary with weather, ambient light, tint in the window glass, moonroof, etc. As an example, the following table gives a comparative look at lighting conditions in some common settings.

| | |
|---|---|
| Mid-day, outdoors | 100,000 lux |
| Dawn, outdoors | 7,000–12,000 lux |
| Inside a car, sunny day | 5000 lux |
| Bright indoors | 2,000–3,000 lux |
| Average home indoors | 500 lux |
| Moonlit night, outdoors | 50 lux |
| Candle light dinner | 10–20 lux |
| Inside a car, night | 5–10 lux |

Based on this table and the average geometry of a driver's compartment, the following requirements must be satisfied by the image acquisition system of the present invention. 1)The monitoring system must be able to function in ambient lighting conditions between 5 lux and 5,000 lux. For the sake of providing a minimally invasive environment, active lighting, if any, must be out of the visible range, preferably infrared. The current camcorder camera can acquire image from a scene with 1 lux illumination, as well as adapting to a wide dynamic range of lighting situations. 2)If a CCD camera is used as an imaging device, the imaging parameters should provide a focussed image of the driver's face from a distance of approximately 50 cm, and the face must fill as much of the image as possible. In other words, to get the best possible resolution on the face and the eyes, the image should contain as little of background as possible. However, the field-of-view of the camera should also be large enough to cover the variation of positions of the driver's face with respect to the camera. 3)The spatial resolution of the camera must be able to resolve the features that contain information on sleepiness. As mentioned in the previous section, these features include the eyelids, and the pupil. 4)The temporal resolution of the camera must be able to resolve the dynamic behavior of the aforesaid features. Specifically, the eyelid should not be smeared during a blink (that can be as brief as one third of a second in normal subjects). Also, it may be needed to detect and measure the rolling motion of the eyeball, through the movements of the pupil.

Based on the dynamic behavior of the eye during sleepiness and sleep onset, the image analysis system of the present invention should satisfy the following requirements. 1)It must be able to locate the eye fast, and track the location continuously over time. Eye localization and tracking should be robust to changes in the shape of the eye because of perspective distortion. If parts of the driver's face are outside the field of view, such as during backing up, looking sideways during lane change, etc., the system must be able to re-locate the eye, once it becomes visible. One of the assumptions is that when a person is close to sleepiness, he or she will tend to be motionless. This is important to the monitoring system of the present invention since at these moments the face images will not change too much so that the system will not lose track. It is possible the system will lose track when a person makes large movement. However, at this moment, the person is supposed to be very conscious. 2)It must be able to detect closing of the eye, and measure the time duration from open to closed states. 3)During the time when the eye is open, it should (preferably) be able to measure the instantaneous velocity of the pupil. 4)Based on the features from (1), (2), and (3), it should be able to decide whether the driver is alert or sleepy. 5)The steps mentioned in item (1), (2), and (3), amount to "feature extraction". The combined "frame rate" for these steps should be high enough so as not to miss the relevant features. 6)The step in item (4), on the other hand, is a "pattern discrimination" task. The processing time for this step will be variable, depending on the behavior of the subject.

The present invention could include several embodiments. One such embodiment as shown in FIG. 1 is as follows. An individual 10 is scanned by a camera 12 which is connected to a processor 14. A small LCD screen 16 with sufficiently high resolution could be included to allow the individual 10 to see his own face and eyes clearly. Also, a controller 18 allows the individual to adjust the camera 12 viewing angle and direction. A track lost-track indicator 20 informs the individual that the camera 12 is off track and needs adjustment by the controller 18. A warning system 22 informs the individual, or some other person or system, of the onset of sleep.

Figure 2:
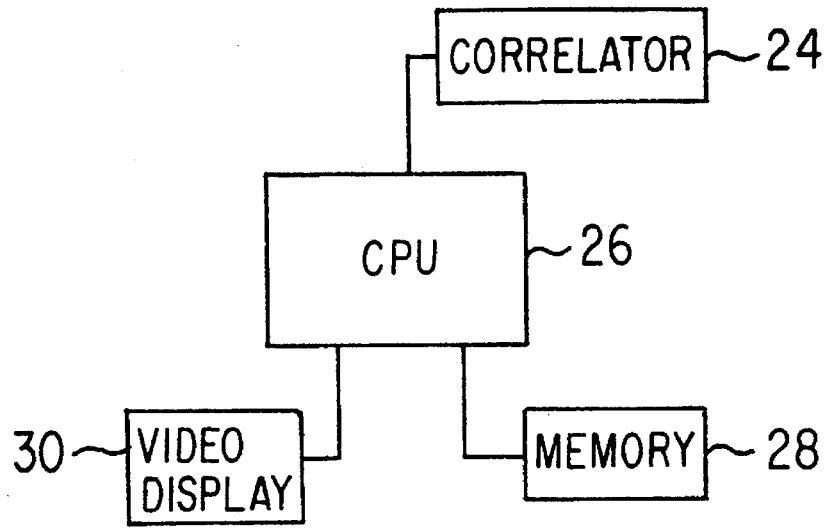

The present invention should be as compact as possible. A customized VLSI chip could be used for the processor 14. The major components of the processor as shown in FIG. 2 include a greyscale correlator 24, a CPU 26 and memory 28. A video display chip 30 is also required for displaying the image on the LCD screen (16 of FIG. 1). The camera, possibly a CCD camera, should be small enough so that it won't block the sight of the driver. The mounting of the camera should have a suspension system to avoid excessive vibrations. The system could also include an ON/OFF switch and a power-on indicator. The power source could be 12V DC if the present invention is integrated into the vehicle or the present invention could be operated by a portable battery if it is a stand alone device. The ideal place in the vehicle to put this device is at the top of dashboard, between the steering wheel and the wind shield screen.

Figure 3:
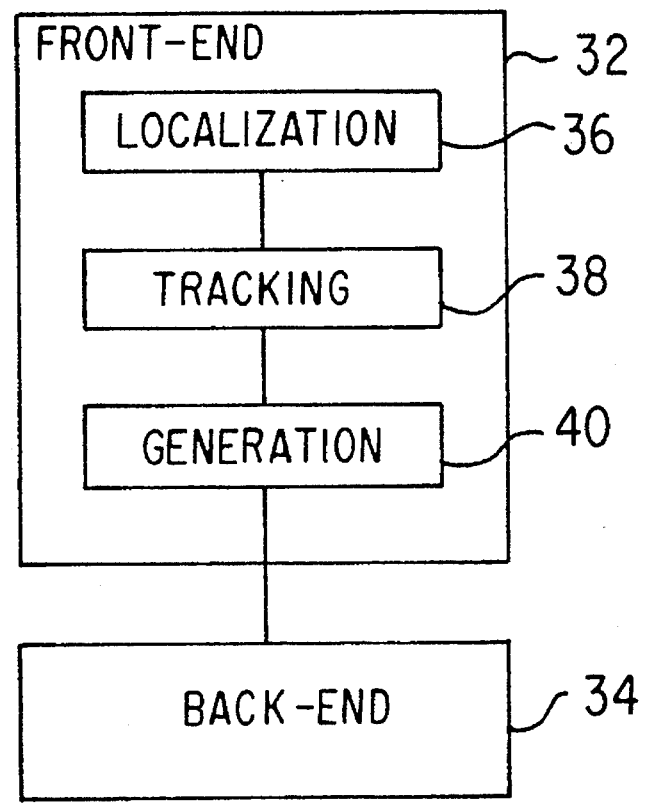

A flow diagram of the processing of the present invention is shown in FIG. 3. The front-end 32, transforms an image sequence to a one dimensional (1-D) signal by extracting relevant features from the images. The back-end 34, analyzes the signal generated from the front-end to detect sleepiness. The front end can be divided into three tasks: eye localization 36, eye tracking 38 and eye motion signal generation 40.

From the assumptions above, it is understood that an image contains a face. How to locate the eye position in this image is a key element of the present invention. Variables are a driver's pose and motion, the lighting conditions, shadows, and bumping on the road. All of these varying conditions will affect the robustness of a method to detect eye position.

Figure 4:
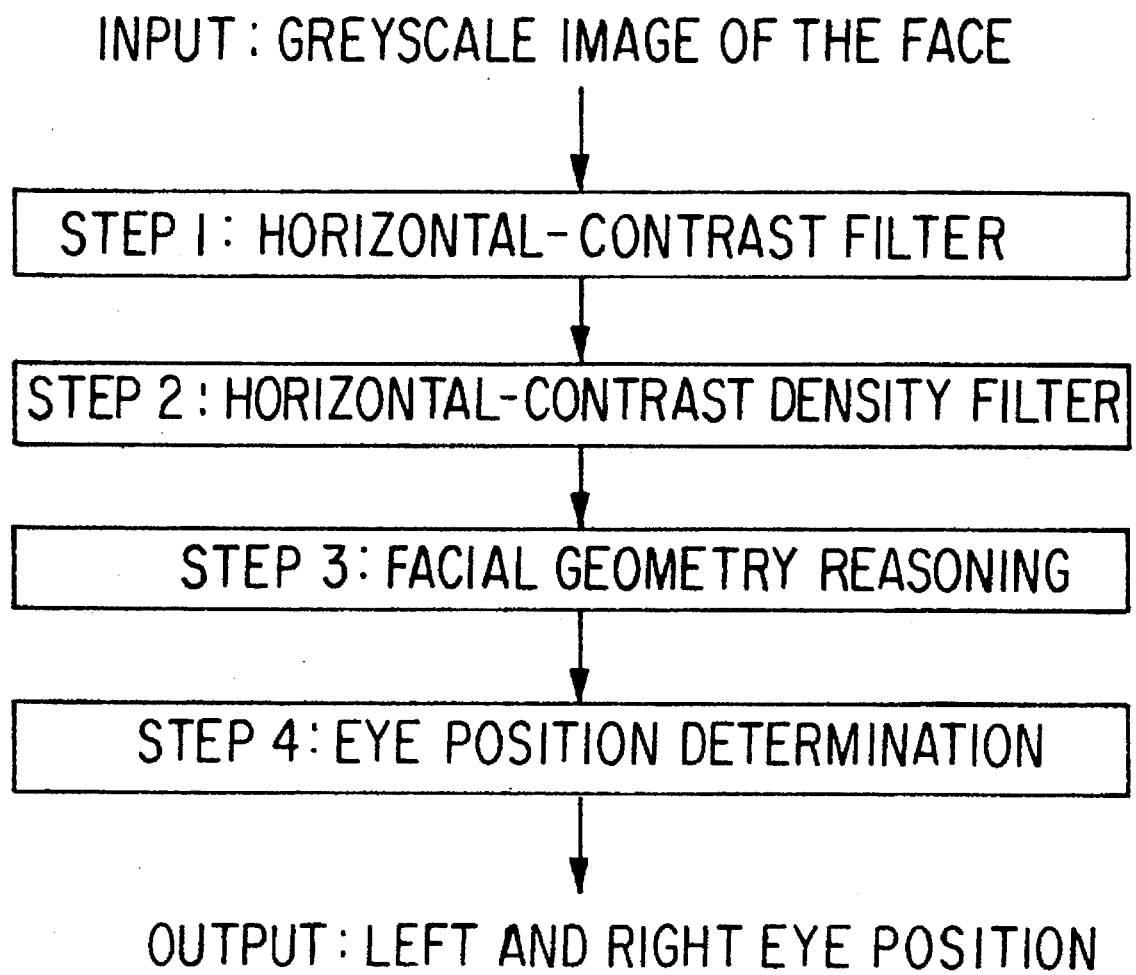
Figure 5A:
Figure 5B:
Figure 5C:
Figure 7:
Figure 7:

The present invention utilizes an eye localization filter as described in copending U.S. Patent Application which is hereby incorporated by reference. The basic idea of this approach is to use the relatively high local intensity contrast of the eye region in greyscale images to locate the eye position. The eye localization filter, as shown in FIG. 4, consists of the following four elements. The greyscale image of the face is sent through a horizontal-contrast filter 42, a horizontal-contrast density filter 44, facial geometry reasoning 46 and eye position determination 48 to establish the left and right eye positions. A typical greyscale image of a face, as shown in FIG. 5(a), is sent through the horizontal-contrast filter and the corresponding output image, the binary mask image, is shown in FIG. 5(b). The binary mask image is sent through the horizontal-contrast density filter and the greyscale mask image, depicting the output of the horizontal-contrast filter is shown in FIG. 5(c). The greyscale mask image is then filtered by the facial geometry reasoning where a-priori information about the geometry of facial features is used to detect and verify eye positions. The results of facial geometry reasoning and the greyscale image are sent through eye position determination which refines the eye positions.

Figure 6:

This filtering takes approximately 200 msec., on a Sparc 10, on a 256×256 pixel image. Twenty images from ten persons under different illuminations and camera viewing directions were used to test this filtering and all eyes were detected correctly. Some experimental results are shown in FIG. 6.

The next major part of the present invention is eye tracking. The detection of eye motion from one frame to the next is achieved by a search process in which an image-block is correlated with the image in the current frame at varying displacements from the original location. This process is discussed in "A Feature Tracking Method For Motion Parameter Estimation In A Model-Based Coding Application", Yau, J. F. S. and Duffy, N. D., 3rd Int. Conf. on Image Processing and its Applications, Warwick, UK, July, 1989, pp. 531–535. The correlation measure used is the sum of the squared differences between the intensities of pixels in the block with the previous image. The image block location giving the minimum value for the correlation measure becomes the new position of the tracked eye. More specifically, let U, an image block of size M×N pixels, be a sub-image from the current frame I(t) and $U_r$ be an (M+2p)× (N+2p) sub-image from the next frame, I(t+1), centered at the same spatial location as U, where p is the maximum displacement allowed in integer number of pixels.

Figure 8:

The correlation function between U and $U_r$ is defined as:

$$D(i,j) = \frac{1}{MN} \sum_{m=1}^{M} \sum_{n=1}^{N} (u(m,n) - u_r(m+i, n+j))^2$$

where $-p \leq i, j \leq p$. D(i,j) is a mean square error function. The direction of minimum error is given by (i,j), for which D(i,j) is a minimum. The parameter p should be selected large enough to cover the most possible large movement. This scheme can track the eye motion for a reasonably large movement such as in the example shown in FIG. 8. The software implementation of this approach on a Sparc 10 takes approximately 800 msec per image (of 256×256 resolution).

Figure 9:
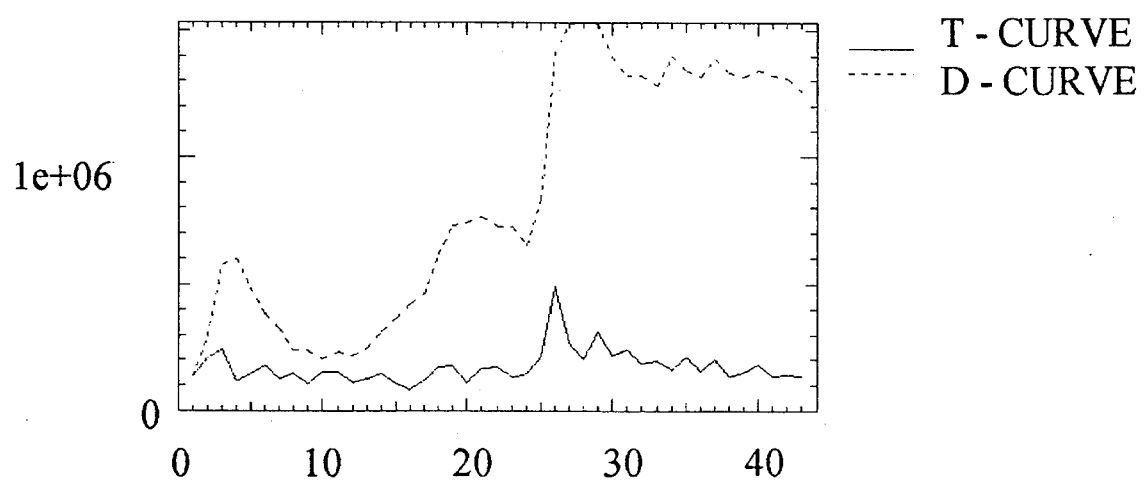

The next major part of the present invention, the last part of the front end of the present invention, is eye motion signal generation. For eye motion signal generation, the technique used in eye tracking, i.e., correlation function, is applied again. However, in this case there is a measurement of the correlation between the new tracked image block in I(t) with the very first initial block in I(O) where the eye is assumed to be open. The D-curve in FIG. 9 is the result of using this measurement on the sequence in FIG. 8. The T-curve in FIG. 9 is the measurement of the difference between the current frame with its previous frame. Since the initial block contains an open eye, a large difference in the D-curve indicates that the eye is closing. The use of the T-curve and D-curve will be further discussed below.

To establish whether the eye is closed or open, the best indicator is the area of the eye. Computation of this feature requires the exact location of the eye boundary. However, if only the blink rate and duration is of interest, the exact boundary of the eye is not so important. An open eye model can be stored as a reference and be used to compare with the rest of the frames in an image sequence. The difference between the reference frame and the current frame is an indicator of the state of the eye. The difference will be small when the eye is open and large when the eye is closed. This indicator does not require the exact boundary of the eye.

All schemes for exact eye boundary localization require very computationally expensive operations either in preprocessing or processing itself. They also require very robust extraction of primitive features from images. The greyscale eye template based approach is simple and effective but it is scale sensitive and lighting sensitive. Multiple frames and channels based approaches provide extra information but have to process two or more times the amount of data with respect to a single frame approach. A combination of different approaches could be used for improving localization of an eye in a robust manner.

In order to address issues related to the back-end of the present invention, the utilization of the graph in FIG. 9 is required. It can be considered as a signal similar to an EEG or EOG signal. It is the visual equivalent that can be used to observe sleepy patterns. This graph contains two different curves. The T-curve shows the tracking and the D-curve indicates the frame difference. One blink around frame 3 or 4 can be observed from the D-curve. At the 25th frame, there is a large jump on both the D-curve and the T-curve. This indicates that the target has had a relatively large movement (In this example, the person leaned backward slightly). A new reference image at this moment may be required in order to obtain a good D-curve for blink detection.

Figure 10:
Figure 10:
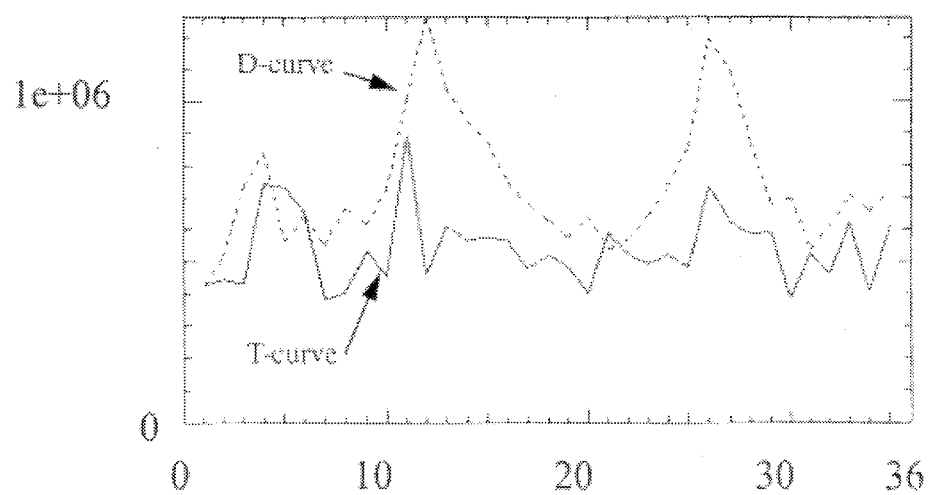
Figure 11:
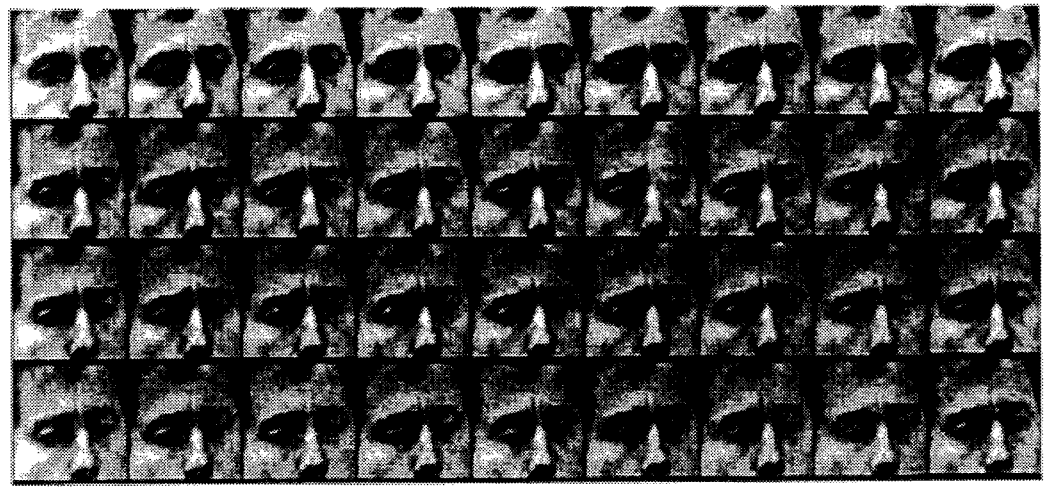
Figure 11:
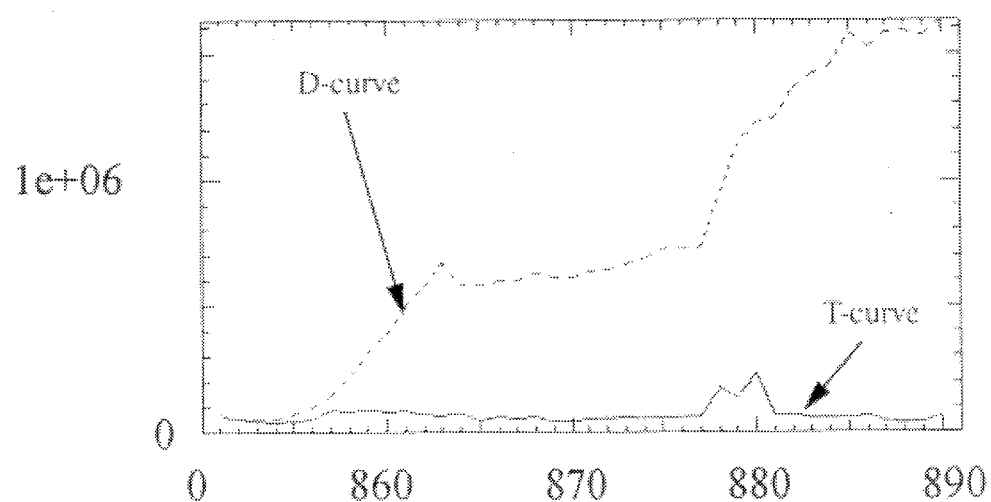

When a person is fighting sleepiness, some of the following patterns will occur. An individual may try to wide-open, blink, or squint the eyes. The blink rates of these patterns are quite different from the blink rates of an awake state. For example, FIG. 10 shows a normal eye blinking and the corresponding T and D curves. FIG. 11 shows a sequence when the person is sleepy and its corresponding T and D curves. By analyzing these curves, it is obvious that there is some difference between these two graphs. When such a difference occurs, a warning signal from a warning system will be sent to the individual. A personal profile, which characterizes the behavior of the person in consideration, could be used to improve the reliability of detection.

When an individual's eyes are covered by sunglasses or glasses with high reflection, special active light sources could be used to penetrate these glasses and special imaging sensors could be used to record the image from the reflected light. One of the requirements of the active light source is that the frequency should be outside of the visible color spectrum. Another alternative is the following. Since the person is wearing glasses, one could put a tiny light source and sensor on the inside rim of the glasses to get a normal image and perform the tracking as described above.

The non-invasive nature of the present invention makes it more attractive for the commercial marketplace. A small camera a few feet away from the driver is far more acceptable as compared to EEG electrodes attached to the driver's head. The eventual market for a non invasive sleepiness/fatigue monitoring system would encompass a wide variety of settings involving monotonous and tiring jobs such as those of assembly line operators, air traffic controllers, airline pilots, medical residents, etc.

It is not intended that the present invention be limited to the hardware or software arrangement, or operational procedures shown disclosed. This invention includes all of the alterations and variations thereto as encompassed within the scope of the claims as follows.

We claim:

1. A system for monitoring eyes for detecting sleep behavior comprising:

human interface means for non-invasive monitoring of said eyes of an individual, for providing scanned images and for providing feedback to said individual; and, processor means connected to said human interface means for receiving said scanned images from said human interface means, for processing said scanned images and for providing processed data back to said human interface means for providing said feedback to said individual, wherein said human interface means comprises:

imaging means connected to said processor means for monitoring said eyes of said individual; and, warning system means connected to said processor means for receiving said processed data from said processor means and for providing a warning to said individual, and wherein said processor means comprises:

eye localization means connected to said human interface means;

eye tracking means connected to said eye localization means;

eye motion signal generation means connected to said eye tracking means; and, analysis means connected between said eye motion signal generation means and said human interface means.

2. A system for monitoring eyes for detecting sleep behavior as claimed in claim 1 wherein said eye localization means comprises:

horizontal-contrast computation filter means;

horizontal-contrast density determination filter means connected to said horizontal-contrast computation filter means;

facial geometry reasoning means connected to said horizontal-contrast density determination filter means; and, eye position determination means connected to said facial geometry reasoning means.

3. A system for monitoring eyes for detecting sleep behavior as claimed in claim 2 wherein said eye tracking means comprises:

search means for correlating an image-block with an image in a current frame at varying displacements from an original location.

4. A system for monitoring eyes for detecting sleep behavior as claimed in claim 3 wherein said eye motion signal generation means comprises:

measurement means for measuring correlation between a new tracked image block and a very first initial block where an eye is open.

5. A system for monitoring eyes for detecting sleep behavior as claimed in claim 4 wherein said analysis means evaluates a tracking T curve and a frame difference D curve.

6. A system for monitoring eyes for detecting sleep behavior as claimed in claim 5 wherein said processor means further comprises:

greyscale correlator means connected to said human interface means.

7. A system for monitoring eyes for detecting sleep behavior as claimed in claim 6 wherein said processor means further comprises:

video display chip means connected to said human interface means.

8. A system for monitoring eyes for detecting sleep behavior as claimed in claim 7 wherein said human interface means further comprises:

controller means connected to said imaging means for allowing said individual to adjust viewing angle and direction of said imaging means.

9. A system for monitoring eyes for detecting sleep behavior as claimed in claim 8 wherein said human interface means further comprises:

track/lost-track indicator means for informing said individual that said imaging means needs adjustment.

10. A system for monitoring eyes for detecting sleep behavior as claimed in claim 9 wherein said imaging means comprises:

a CCD camera.

11. A method of monitoring eyes for detecting sleep behavior comprising the steps of:

noninvasively monitoring said eyes of an individual;

providing scanned images;

processing said scanned images; and, providing feedback to said individual, wherein the step of processing said scanned images comprises the steps of:

localizing said eyes;

tracking said eyes;

generating eye motion signals; and, analyzing said eye motion signals, and wherein the step of localizing said eyes comprises the steps of:

horizontal-contrast computation filtering of a greyscale image of a face for providing a binary mask image;

horizontal-contrast density determination filtering of said binary mask image for providing a greyscale mask image;

performing facial geometry reasoning on said greyscale mask image for providing approximate positions of two eyes; and, performing eye position determination of said greyscale image of a face and said approximate positions of two eyes for providing positions of two eyes.

12. A system for monitoring eyes for detecting sleep behavior comprising:

human interface means; and, processor means connected to said human interface means wherein said processor means comprises:

greyscale correlator means connected to said human interface means;

eye localization means connected to said greyscale correlator means;

eye tracking means connected to said eye localization means;

eye motion signal generation means connected to said eye tracking means; and, analysis means connected between said eye motion signal generation means and said human interface means.

13. A system for monitoring eyes for detecting sleep behavior as claimed in claim 12 wherein said human interface means comprises:

imaging means connected to said greyscale correlator means for monitoring said eyes of an individual; and, warning system means connected to said analysis means for receiving analyzed data from said analysis means and for providing a warning to said individual.

14. A system for monitoring eyes for detecting sleep behavior as claimed in claim 13 wherein said human interface means further comprises:

controller means connected to said imaging means for allowing said individual to adjust viewing angle and direction of said imaging means; and, track/lost-track indicator means for informing said individual that said imaging means needs adjustment.

15. A system for monitoring eyes for detecting sleep behavior as claimed in claim 15 wherein said processor means further comprises:

video display chip means connected to said human interface means.

16. A system for monitoring eyes for detecting sleep behavior as claimed in claim 19 wherein said eye localization means comprises:

horizontal-contrast computation filter means;

horizontal-contrast density determination filter means connected to said horizontal-contrast computation filter means;

facial geometry reasoning means connected to said horizontal-contrast density determination filter means; and, eye position determination means connected to said facial geometry reasoning means.

* * * * *

UNITED STATES PATENT AND TRADEMARK OFFICE
CERTIFICATE OF CORRECTION

PATENT NO. : 5,570,698

DATED : Nov. 5, 1996

INVENTOR(S) : Liang et al.

It is certified that error appears in the above-identified patent and that said Letters Patent is hereby corrected as shown below:

Column 10

Line 24, delete: "15" and insert in its place: --14--.

Line 29, delete: "19" and insert in its place: --15--.

Signed and Sealed this

First Day of April, 1997

Attest:

BRUCE LEHMAN

Attesting Officer

Commissioner of Patents and Trademarks